US006824759B2

(12) United States Patent
Thakur et al.

(10) Patent No.: US 6,824,759 B2
(45) Date of Patent: Nov. 30, 2004

(54) RADIOLABELED VASOACTIVE INTESTINAL PEPTIDE ANALOGS FOR IMAGING AND THERAPY

(75) Inventors: Madhukar L. Thakur, Cherry Hill, NJ (US); M. V. Ramana Reddy, Upper Darby, PA (US)

(73) Assignees: Thomas Jefferson University, Philadelphia, PA (US); Temple University - of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 10/100,256

(22) Filed: Mar. 15, 2002

(65) Prior Publication Data

US 2003/0152511 A1 Aug. 14, 2003

Related U.S. Application Data

(62) Division of application No. 09/333,842, filed on Jun. 15, 1999, now Pat. No. 6,395,255.
(60) Provisional application No. 60/089,364, filed on Jun. 15, 1998.

(51) Int. Cl.[7] .................. A61K 51/00; A61M 36/14
(52) U.S. Cl. .................. 424/1.69; 424/1.11; 424/1.65; 424/9.1; 530/324
(58) Field of Search .................. 424/1.11, 1.65, 424/1.69, 9; 534/7, 10–16; 530/300, 324

(56) References Cited

U.S. PATENT DOCUMENTS 5,849,261 A * 12/1998 Dean et al. ............. 424/1.69
6,126,916 A * 10/2000 McBride et al. .......... 424/1.69

OTHER PUBLICATIONS

Pallela et al., J. Nucl. Med. 39:226P, 1998., Abstract No. 999.

* cited by examiner

*Primary Examiner*—Dameron L. Jones
(74) *Attorney, Agent, or Firm*—Drinker Biddle & Reath LLP

(57) ABSTRACT

This invention relates to a radiodiagnostic agent to image tumors. A composition for a tumor imaging agent, a method and kit for preparing a tumor imaging agent, and a radiolabeling reagent for preparing the tumor imaging agent are provided. Methods of using the tumor imaging agent to detect tumors are also provided

8 Claims, 6 Drawing Sheets

His-Ser-Asp-Ala-Val-Phe-Thr-Asp-Asn-Tyr-Thr-Arg-Leu-Arg-Lys-Gln-Met-Ala-
Val-Lys-Lys-Tyr-Leu-Asn-Ser-Ile-Leu-Asn-Aba-Gly-Gly-(D)Ala-Gly-(Resin)

↓ (i)

His-Ser-Asp-Ala-Val-Phe-Thr-Asp-Asn-Tyr-Thr-Arg-Leu-Arg-Lys-Gln-Met-Ala-
Val-Lys-Lys-Tyr-Leu-Asn-Ser-Ile-Leu-Asn-Aba-Gly-Gly-(D)Ala-Gly

↓ (ii)

His-Ser-Asp-Ala-Val-Phe-Thr-Asp-Asn-Tyr-Thr-Arg-Leu-Arg-Lys-Gln-Met

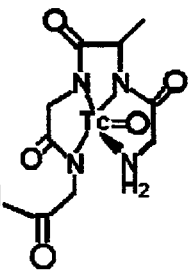

Ala-Val-Lys-Lys-Tyr-Leu-Asn-Ser-Ile-Leu-Asn-Aba*-CO-NH

\* 4-aminobutyric acid (i) TFA / Thioanisole / Ethanedithiol / Phenol (90 : 5 : 3 : 2)
(ii) Na$^{99m}$TcO$_4$ /SnCl$_2$ /Na$_3$PO$_4$ (PH 12)

Fig. 1

SEQUENCE LISTING

```
<160> NUMBER OF SEQ ID NOS: 3

<210> SEQ ID NO 1
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 1

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 2
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 29
<223> OTHER INFORMATION: Xaa = D-4-aminobutyric acid (4-abu)
<220> FEATURE:
<221> NAME/KEY: VARIANT
<222> LOCATION: 32
<223> OTHER INFORMATION: alanine is D-alanine

<400> SEQUENCE: 2

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn Xaa Gly Gly Ala
            20                  25                  30

Gly

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 2
<223> OTHER INFORMATION: alanine is D-alanine

<400> SEQUENCE: 3

Gly Ala Gly Gly
 1
```

RADIOLABELED VASOACTIVE INTESTINAL PEPTIDE ANALOGS FOR IMAGING AND THERAPY

CROSS REFERENCE TO RELATED APPLICATIONS

This application is a Divisional application of U.S. Non-provisional patent application Ser. No. 09/333,842, filed Jun. 15, 1999, now U.S. Pat. No. 6,395,255, which claims priority based under 35 U.S.C. §119 based upon U.S. Provisional Patent Application No. 60/089,364, filed Jun. 15, 1998.

FIELD OF THE INVENTION

This invention relates generally to the field of nuclear medicine and, more particularly to, radiolabeled agents for imaging tumors, methods of use of said agents, and kits for preparing imaging agents.

BACKGROUND OF THE INVENTION

Cancer remains a major health problem among humans. In the United States colorectal cancer is the second most common cancer in women after breast cancer, and the third most common cancer in men after prostate and lung cancer. While the colorectal cancer incidence rates for white and black males are similar (roughly 61 per 100,000 population), the rate for white females (88 per 100,000 population) is higher: than that for black females (79 per 100,000 population). However, the mortality rate for both black males and black females is higher than their white counterparts, suggesting that late diagnosis may contribute to the mortality rate. Moreover, in that the incidence and mortality rates related to this disease continue to rise, the need for early diagnosis is of undisputed importance for management of the cancer. (Scottenfeld, D., Cancer of the Colon, Rectum and Anus, Chapter 3, Epidemiology, Cohen, A. (Ed.), McGraw Hill, Inc., New York, 1993, pp. 11–24). If the diagnosis is made while the cancer is still silent or occult, the cancer may be treated with conservative surgery, with or without additive, radio- or chemotherapy.

During the past 15 years, advances have been made in diagnostic imaging of tumors. The introduction of computerized tomography (CT) by Hounsfield in the early 1970's, enabled more accurate detection with higher spatial resolution for small foci of cancer than previous x-ray technology. Similarly, magnetic resonance imaging (MRI) improved the diagnostic capabilities for detecting bone malignancies.

Gamma cameras have generally been used for diagnostic purposes because they are considerably less expensive than either CT or MRI scanners, and the scintigraphic studies are more cost effective than the CT or MRI imaging. Gamma cameras enable a patient's entire body to be scanned at one time and in a relatively short period, allowing a single diagnostic test to be utilized for all imaging needs. However, while nuclear medicine can facilitate the diagnosis of cancer, there remains a need for better imaging techniques and more specific imaging agents for detecting tumors, particularly those that have metastasized.

Recently, CT, MRI and ultrasound imaging have been criticized for the detection of colorectal adenocarcinoma. (Beutow, P. C. et al., Radiographics 15: 127–146, 1995). The manner of routine screening for this disease remains controversial, and it is generally agreed that CT should not be used routinely to stage colorectal carcinoma because of its low accuracy. In that the five year survival rate patients with colorectal cancer is only 5%, and that this rate has not changed for the past 40 years, it is evident that the early detection of small cancers and pre-malignant adenomas is necessary to improve the survival rate. For early detection to be practical, new non-invasive methods of detection of this disease are necessary.

Biomolecules specific for tumor antigens, when labeled with gamma emitting radionuclides, can provide an efficient means of detecting lesions. Oncoscint, an In-111 labeled anti-CEA and anti-TAG-72 antibody, has been utilized as a tumor imaging agent. However, this agent has had only limited success because of relatively low sensitivity (40%) and specificity (50%) (Beatty, J. D. et al., Cancer of the Colon, Rectum and Anus, Radioimmunoscintigraphy, Chapter 77, Cohen, A. (Ed.), McGraw Hill, Inc., New York, 1993, pp. 753–767; John, T. M. et al., Proc. Annu. Mtg. Am. Soc. Clin. Oncol. 13: A275, 1994), and because it induces an immunologic reaction in 30% of the patients. (Corman, M. L. et al., Diseases of the Colon and Rectum 37: 129–137, 1994). The imaging agent is also of limited because of its high liver uptake which precludes its use for detecting liver metastases. (Abdel-Nabvi, H. H. et al., Targeted Diag. and Therapy 6: 78–88, 1992). Agents with improved specificity and sensitivity, and ones that can be used reliably to detect liver metastases would be widely accepted by clinicians.

Radiolabeled receptor peptides specific for imaging tumors, abscesses and vascular thrombi are particularly attractive for use as radioimaging agents because they are smaller in size, easier to produce, and cleared more rapidly from the blood than other receptor specific larger molecules, such as radiolabeled monoclonal antibodies. In-111-Octreotide, a radiolabeled somatostatin analog, has been used to image endocrine tumors. However, it does not appear that this imaging agent is as sensitive as an I-123 labeled vasoactive intestinal peptide (VIP). Only four positive scans were obtained in 17 patients with colonic adenocarcinoma using In-111-Octreotide, as compared to 17 out of 17 positive scans with I-123 labeled VIP. (Virgolini, I. et al., New Eng. J. of Med. 33: 1116–21, 1994).

VIP is a 28 amino acid neuroendocrine mediator that has been detected on the cell surface membrane of intestinal epithelial cells (Virgolini, I. et al., Cancer Res. 54: 690–700, 1994; Blum, A. M. et al., J. Neuroimmunol. 39:101–8, 1992), lungs (Couvineau, A. et al., J. Clin. Endocrinol., Metab. 61: 50–55, 1985), and various tumor cells, including colonic adenocarcinomas (el Battari, A. et al., J. Biol. Chem. 263: 17685–9, 1988), pancreatic carcinomas (Svoboda, M. et al., Eur. J. Biochem 176: 707–13, 1988) and carcinoids (Virgolini, I. et al., Cancer Res. 54: 690–700, 1994). The amino acid sequence for VIP, which is identical for porcine, bovine, dog and human, is His Ser Asp Ala Val Phe Thr Asp Asn Tyr Thr Arg Leu Arg Lys Gln Met Ala Val Lys Lys Tyr Leu Asn Ser Ile Leu Asn (SEQ ID NO: 1). It was initially isolated from porcine intestine more than 25 years ago. (Said, et al., Science 69: 1217–1218, 1970).

When labeled with I-123, VIP has been shown to be effective in imaging colorectal adenocarcinoma (100%), including in patients with liver metastases (83%). However, the lung uptake of this agent is very high: approximately 25% at four hours post-injection and 10% at 24 hours post-injection. It is unclear at present whether or not the high lung uptake is related to lung receptor density or to iodination of the two tyrosine residues (residues 10 and 22 of VIP). Accordingly, iodinated VIP adversely affects imaging of lung metastases (66%).

Further, although I-123 is widely used for scintigraphic imaging, and may be a logical choice to label a tyrosine containing peptide, it is a cyclotron produced radionuclide with a relatively short half-life (13.3 hours). It is therefore expensive to produce, and must be ordered within 24 hours of its intended use to prevent excessive radioactivity decay. For these reasons I-123 has not been widely utilized for clinical applications.

Conversely, Technetium-99m ("Tc-99m"), is produced on a generator from its parent radionuclide Molydenum-99 ("Mo-99"), which has a substantially longer half-life (2.8 days). Mo99, bound on solid matrix in several mCi quantities, can be purchased once a week. The Tc-99m is washed off with sterile isotonic saline once or twice a day as needed. Tc-99m decays within a six hour half-life with the emission of 140 keV gamma rays. The shorter half-life permits rapid decay of the radioactivity, minimizes the radiation dose to normal organs, and eliminates the need for patient hospitalization. Its gamma ray energy also allows efficient detection by gamma cameras. Further, because of the generator system, the radionuclide is relatively inexpensive. For these reasons Tc-99m has become the radionuclide of choice in nearly 90% of the clinical nuclear medicine applications.

It has now been found that a modification of the peptide sequence His Ser Asp Ala Val Phe Thr Asp Asn Tyr Thr Arg Leu Arg Lys Gln Met Ala Val Lys Lys Tyr Leu Asn Ser Ile Leu Asn (SEQ ID NO: 1) can be used to image tumors, particularly colonic adenocarcinomas, liver metastases, pancreatic carcinomas, and carcinoids.

SUMMARY OF THE INVENTION

The present invention provides a composition useful as a radiodiagnostic agent for imaging tumors, particularly endocrine tumors, liver metastases, and carcinoids in mammals, a method and a kit for the preparation of the tumor imaging agent, a reagent for radiolabeling the imaging agent, and a method of use for the tumor imaging agent. Specifically, the tumor imaging agent is comprised of a composition containing a tumor specific sequence (TSS) and a radionuclide moiety linked to the TSS via a linker, wherein a radionuclide is complexed to the radiolabeling moiety. In a preferred embodiment, the composition comprises the sequence His Ser Asp Ala Val Phe Thr Asp Asn Tyr Thr Arg Leu Arg Lys Gln Met Ala Val Lys Lys Tyr Leu Asn Ser Ile Leu Asn Xaa Gly Gly (D)Ala Gly (SEQ ID NO: 2).

A second embodiment of the invention provides a reagent for radiolabeling a TSS, comprising four amino acids, selected from the group consisting of glycine and alanine, which can covalently link a selected radionuclide to the amino groups of each amino acid to form an $N_4$ configuration.

Still another embodiment of the invention provides a kit for preparing a thrombus imaging agent, which kit comprises a container capable of holding a multiple of vials and reagents. A first vial contains an appropriate quantity of prepared TSS and radionuclide moiety for reacting with a radionuclide. A second vial contains an appropriate buffer, The invention also provides a method of imaging endocrine tumors in a mammal by obtaining in vivo gamma scintigraphic images. The method comprises administering an effective diagnostic amount of the thrombus imaging agent to a mammal in need of such imaging and detecting the gamma radiation emitted by the imaging agent localized at the thrombus site within the mammal.

DESCRIPTION OF THE FIGURES

FIG. 1 is a structural representation of a tumor imaging agent.

DETAILED DESCRIPTION OF THE INVENTION

Abbreviations and Definitions

1. Abbreviations

Figure 2:
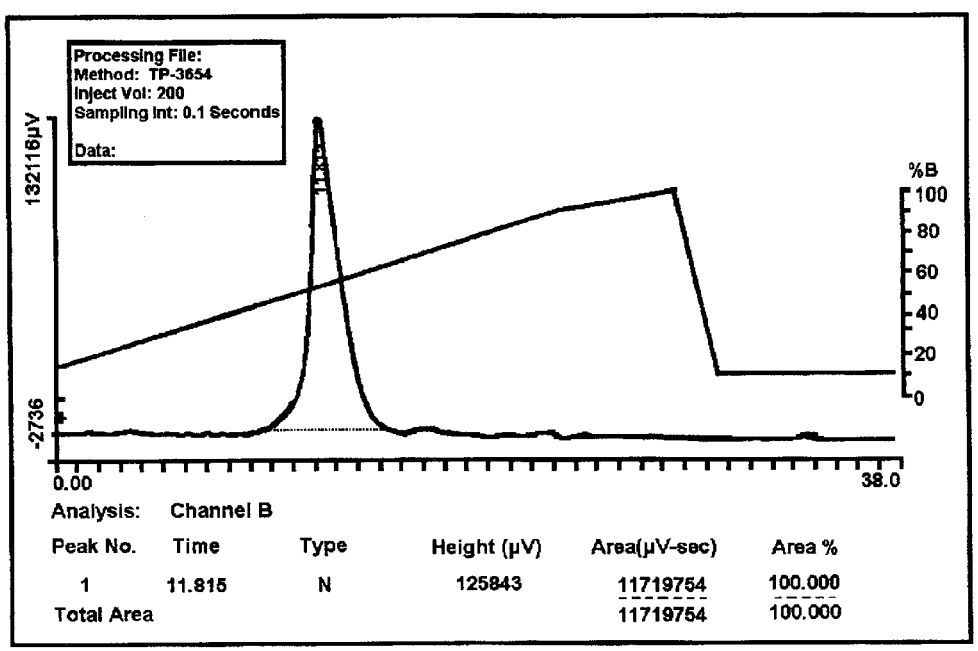
FIG. 2 is the HPLC elution profile of $^{99m}$Tc-TP3654. One hundred percent radioactivity is eluted in single peak at Rt 11.8 min. This is considerable improvement over multiple peaks with CPTA-VIP and MAG$_3$-VIP analogs. A diagonal line represents gradient composition.

| | |
|---|---|
| Aba | 4-aminobutyric acid |
| ADP | Adenosine 5'-diphosphate |
| CPTA | (4-(1, 4, 8, 11-tetraazacyclotetradec-1-yl)methyl) benzoic acid |
| LS174T | Human colorectal tumor cell line |
| MAG$_3$ | (N-(N(N-(benzylthio)acetyl)glycyl)glycyl)glycin |
| TFA | Trifluoroacetic acid |
| TSS | Tumor specific sequence |
| VIP | Vasoactive intestinal peptide |
| Xaa | 4-aminobutyric acid |

2. Definitions

"Natural amino acid" means any of the twenty primary, naturally occurring amino acids which typically form peptides and polypeptides. By "synthetic amino acid" is meant any other amino acid, regardless of whether it is prepared synthetically or derived from a natural source.

"Radiolabeling moiety" is a sequence comprising four amino acids capable of complexing with a selected radionuclide in an $N_4$ configuration.

"Radiolabeled complex" is the complex formed by the radiolabeling moiety and the selected radionuclide.

"Technetium" refers to the radioactive form of technetium, for example, technetium-99m (Tc-99m).

"Tumor imaging agent" refers to a radiolabeled TSS to be used as a radiodiagnostic agent.

"Tumor specific sequence ("TSS")" refers to a peptide with the sequence His Ser Asp Ala Val Phe Thr Asp Asn Tyr Thr Arg Leu Arg Lys Gln Met Ala Val Lys Lys Tyr Leu Asn Ser Ile Leu Asn (SEQ ID NO: 1) or an analog or fragment thereof, to which one or more natural or synthetic amino acids and a linker have been added to the NH$_2$ or COOH termini.

Tumor Imaging Agents

This invention is directed to a radiodiagnostic agent to image tumors in a mammal. The invention provides a composition useful as a tumor imaging agent, a method and kit for preparing the tumor imaging agent, and a radiolabeling reagent for preparing the tumor imaging agent. Tumors as described refers to tumors that express the VIP receptor, including, but not limited to, breast, ovarian, endometrial, prostate, bladder, lung, esophageal, colonic and pancreatic cancers, and neuroendocrine and brain tumors.

The tumor imaging agent is a composition for imaging tumors in a mammal having the formula of I or II:

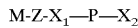    (I)

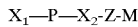    (II)

wherein:

M is a radiolabeling moiety comprised of four amino acids capable of complexing with a selected radionuclide in an $N_4$ configuration;

Z is a linker comprised of one or more natural or synthetic amino acids;

$X_1$ and $X_2$ are from zero to twenty natural or synthetic amino acids; and

P is a peptide comprising the sequence His Ser Asp Ala Val Phe Thr Asp Asm Tyr Thr Arg Leu Arg Lys Gln Met Ala Val Lys Lys Tyr Leu Asn Ser Ile Leu Asn (SEQ ID NO: 1), or an analog or fragment thereof, wherein a radionuclide is complexed to the radiolabeling moiety, M of the composition of formula (I) or (II). In a preferred embodiment the composition comprises His Ser Asp Ala Val Phe Thr Asp Asm Tyr Thr Arg Leu Arg Lys Gln Met Ala Val Lys Lys Tyr Leu Asn Ser Ile Leu Asn Xaa Gly (D)Ala Gly Gly (SEQ ID NO: 2) or analog or fragment thereof.

The tumor imaging agent is comprised of a TSS and a radiolabeled complex connected by the linker of the TSS. By "TSS" it is meant a peptide with the sequence, His Ser Asp Ala Val Phe Thr Asp Asm Tyr Thr Arg Leu Arg Lys Gln Met Ala Val Lys Lys Tyr Leu Asn Ser Ile Leu Asn (SEQ ID NO: 1) or an analog or fragment thereof, to which one or more natural or synthetic amino acids and a linker have been added to the $NH_2$ and/or COOH termini. The linker comprises one or more natural or synthetic amino acids that will preserve the biological activity of the peptide sequence from any steric hindrance imparted by the use of the radionuclide moiety. Preferably, the TSS is comprised of from about 28 to about 50 amino acids, more preferably from about 28 to about 40 amino acids, and most preferably, from about 28 to about 30 amino acids.

In a preferred embodiment the linker, 4-aminobutyric acid Xaa, has been added to the COOH terminus of a sequence, such as SEQ ID NO: 2. Alternatively, one or more amino acids and a linker could be added to the $NH_2$ terminus.

Analogs of the peptide of the TSS can also be utilized in the invention. By "analog" is meant a derivative or modification of the native sequence. One skilled in the art may prepare such analogs wherein the native sequence is modified by resultant single or multiple amino acid substitutions, additions or deletions. All such modifications resulting in a derivative TSS are included within the scope of the invention, provided that the molecule binds to the tumor and thereby, acts as a tumor imaging agent when radiolabeled.

Conservative amino acid changes may be made which do not alter the biological function of the native sequence. For instance, one polar amino acid, such as threonine, may be substituted for another polar amino acid, such as serine; or one acidic amino acid, such as aspartic acid, may be substituted for another acidic amino acid, such a glutamic acid; or a basic amino acid, such as lysine, arginine or histidine, may be substituted for another basic amino acid; or a non-polar amino acid, such as alanine, leucine or isoleucine, may be substituted for another non-polar amino acid.

Accordingly, an analog as described herein corresponds not only to the native peptide described herein, but also to any analog or fragment thereof which retains the essential biological activity of the peptide. Analogs include any peptide having an amino acid sequence substantially similar to that of SEQ ID NO: 2 in which one or more amino acids have been substituted or inserted in the native sequence. Fragments include peptides of the length less than the full length of SEQ ID NO: 2. The practice of the present invention is, thus, not limited to sequences of the same length as SEQ ID NO: 2, but also includes such fragments of this TSS, provided they bind to the tumor when complexed with the radiolabel moiety and thus, act when radiolabeled as a tumor imaging agent. Whether an analog or fragment retains the biological activity of the native TSS may be determined by those skilled in the art by following the experimental protocols set forth in herein.

Another embodiment of the invention is the preparation of a radiolabeling moiety for use as a reagent in the production of a thrombus imaging agent. The radiolabeling moiety is capable of complexing with a radionuclide in an $N_4$ configuration. An $N_4$ configuration is one in which the radionuclide is linked to each amino acid through its $NH_2$ group. While the $N_4$ configuration is a preferred embodiment for the present invention, other configurations are included within the practice of the present invention. Thus, radiolabeled complexes in which a radionuclide such as technetium is joined to a single thiol moiety or two amino and two thiol moieties ($N_2S_2$ configuration) are equivalent to the $N_4$ configuration.

For the preparation of the radiolabeled complex as described herein, four amino acids (the radiolabeling moiety) are covalently linked (or complexed) to a selected radionuclide. Preferably, the amino acids ore independently selected from the group consisting of glycine and alanine, provided that at least three of the amino acids are glycine. Alternatively, any combination of amino acids that form an $N_4$ configuration can be utilized within the scope of this invention. Amino acids of both the D and L enantiomeric configuration can be employed herein. Naturally occurring or synthetic amino acids can be employed herein. In a preferred embodiment, the sequence for the radiolabeling moiety is Gly (D)Ala Gly Gly (SEQ ID NO: 3).

In a preferred embodiment technetium-99m is selected as the radionuclide. However, examples of other suitable radionuclides which can be complexed with this moiety include, but are not limited to, Re-186, Re-188, In-111, Ga-67, Ga-68, Tl-201, Fe-52, Pb-203, Co-58, Cu-64, I-123, I-124, I-125, I-131, At-210, Br-76, Br-77 and F-18.

Another embodiment of the invention is the use of the tumor imaging agent to image tumors in mammals, preferably humans. A protocol for such use is provided in Example. Tumor imaging agents of the invention are administered to a mammal in need of such imaging, i.e., suspected of having a tumor, by intravenous injection. The tumor imaging agent is administered in a single unit injectable dose at a concentration which is effective for diagnostic purposes. The tumor imaging agent is administered intravenously in any conventional medium, such as isotonic saline, blood plasma, or biologically compatible isotonic buffers, such as phosphate, Hepes or Tyrode's buffer. Generally, the unit dose to be administered has a radioactivity of about 0.01 to about 100 mCi, preferably about 1 to 40 mCi. The solution amount to be injected as a unit dose is from about 0.1 ml to about 50.0 ml. Preferably, the amount injected is from about 0.5 to about 5 ml (same thing). Imaging of the tumor can take place within a few minutes of injection. However, imaging can take place, if desired, several hours after injection. In most instances, a sufficient amount of the administered dose will accumulate in the desired area within a few minutes to a few hours after injection to permit the taking of scintigraphy images. This is an "effective diagnostic amount". Any conventional method of scintigraphic imaging, planar, SPECT or PET, for diagnostic purposes, can be utilized in accordance with this invention.

Still another embodiment of the invention is a kit for the preparation of the tumor imaging agent. An example of such a kit is provided in Example. The kit includes a carrier for holding the kit components and containers of the TSS, reducing agent and buffer.

The methods for making and using the tumor imaging agent of the invention are more fully illustrated in the following examples. These examples illustrate certain aspects of the above-described invention and are shown by way of illumination and not by way of limitation.

EXAMPLES

Preparation of Tumor Imaging Agent

The tumor imaging agent of the invention described herein was prepared according to the following protocols.

Preparation of Composition of Formula (I) or (II)

The composition corresponding to the peptide His Ser Asp Ala Val Phe Thr Asp Asn Tyr Thr Arg Leu Arg Lys Gln Met Ala Val Lys Lys Tyr Leu Asn Ser Ile Leu Asn Xaa Gly (D)Ala Gly Gly (SEQ ID NO: 2) was prepared using Wang resin and an automated synthesizer (Applied Biosystems Inc., Model No. 430). The peptide was cleaved from the resin with 90% TFA and precipitated by the addition of diethylether at −20° C. The peptide was purified using preparative high-performance liquid chromatography (HPLC; Shimadzu LC-10 AD Columbia, Md.) and a 5-• $C_{18}$ HAlsil column. Fractions were collected and lyophilized, and the resultant compounds were characterized using a Perkin Sciex APZ ion-spray mass spectrometer (Norwalk, Conn.). The peptide with the linker and the four amino acids comprising the radiolabeling moiety had the observed molecular weight of 3654.48, as compared to the theoretically expected weight of 3654.32. This analog is referred to as TP3654. The chemical aspects of this preparation have been described elsewhere, the details of which are incorporated by reference herein. (Pallela et al., J Nucl Med. 39: 226P, 1998).

Preparation of $^{125}$I-VIP and $^{125}$I-TP3654

Both VIP and TP3654 contain two tyrosine residues (positions 10 and 22) and facilitate radioiodination, as demonstrated previously. (Virgolini et al., N Engl J Med. 331:1116–1121, 1994). In brief, 100 •g iodogen in 10 •L $CHCl_3$ was placed in a clean, siliconized, conical glass vial, and chloroform was evaporated by a gentle stream of nitrogen. Then, 10 •g VIP or TP3654 in 10 •L 0.5 mol/L phosphate buffer, ph 7.5, was added, followed by approximately 1 mCi ($^{125}$I)NaI solution in approximately 100 •L 0.5 mol/L phosphate buffer, pH 7.5. The vial was sealed, and the solution was mixed in a vortex mixer and allowed to react for 30 min at 22° C. The reaction was terminated by adding 500 •g sodium metabisulfite. The product was purified using a Rainin 4.6 mm×25 cm, $C_{18}$(5-•) microbond reverse-phase column (Woburn, Mass.) connected to a Rainin HPLC equipped with NaI (Tl) radioactivity detector and an ultraviolet monitor. The eluting solvent consisted of 0.1% TFA in water (solvent A) and 0.1% TFA in acetonitrile (solvent B) at a flow rate of 1 mL/min. The mono-iodinated VIP or TP3654 was collected and solvent evaporated, and then the $^{125}$I-VIP or $^{125}$I-TP3654 was taken up in a suitable volume of 0.1 mol/L tris(hydroxymethyl)aminomethane (Tris) buffer, pH 10, containing 0.1% human serum albumin (HSA) and stored at −80° C. On one occasion, $^{125}$I-VIP was purchased from Amersham Life Sciences (Buckinghamshire, UK).

Preparation of $^{99m}$Tc-TP3654

To a clean, nitrogen-flushed, 10-mL glass vial was added 50 •g TP3654 in acetate buffer (pH 4.6), 50 •g $SnCl_2 \times H_2O$ in 10 •L 0.005 mol/L HCl and 300 •L 0.1 mol/L trisodium phosphate (pH 12.0). The content was frozen immediately by placing the vial in an acetone dry-ice bath. The vial was then placed in a GeneVac lyophilizer (Sheffield, UK) and was lyophilized for 2 h. The vials were then filled with nitrogen, sealed and stored at −20° C.

To a vial at 22° C., 10–40 mCi $^{99m}$Tc in 0.1-0.6 mL 0.9% NaCl was added and mixed using a vortex mixer. The mixture was incubated for 15 min. Then, the pH of the reaction mixture was raised to 6–6.5 by the addition of 1–1.5 mL 0.1 mol/L $Na_2HPO_4$ solution, pH 5.2. Ascorbic acid (500 •g) was then added as a stabilizing agent. HPLC analysis was performed using a Rainin HPLC with a reverse-phase $C_{18}$ microbond column and with 0.1% TFA in $H_2O$ (solvent A) and 0.1.% TFA in acetonitrile (solvent B). The gradient was such that solvent B was 10% at 0 min and 90% at 28 min. In instant thin-layer chromatography (ITLC-SG; Gelman Sciences, Ann Arbor, Mich.) using pyridine:acetic acid:water (3:5:1.5) as a mobile phase, colloid remains at Rf 0.0 and $^{99m}$Tc-TP3654 migrates at Rf 1.0.

Stability of $^{99m}$Tc-TP3654

To measure the in vitro stability of $^{99m}$Tc-TP3654, a known quantity of the preparation was incubated at 37° C. for 24 h, with 100 molar excess of DTPA, HSA or cysteine. At 0, 5 and 24 h, samples were withdrawn for HPLC analysis and the radioactivity that was associated with the challenging agent and that remained as $^{99m}$Tc-TP3654 (Rt= 11.8 min) was measured.

Functional Assay Using Opossum Anal Sphincter Smooth Muscle Tissues

This assay was performed by using the method of Rattan and colleagues (Chakder, S. et al., J Pharm Exp Therapeut. 266:392–399, 1993; Moummi, C. et al., Am J Physiol. 1988;255:G571-G578) to examine the biological activity of TP3654 and CPTA-VIP. Native $VIP_{28}$ was used as a control. Multiple lines of evidence suggest that VIP is on eof the inhibitory neurotransmitters in the gut. The assay is based on the binding of VIP to specific receptors that cause a decrease in the resting tension of the internal anal sphincter (IAS) smooth muscle. This was determined in the presence of increasing concentrations of VIP until maximum fall was reached.

Preparation of Smooth Muscle Strips

Adult opossums (Didelphis virginiana) of either sex were anesthetized with pentobarbital (40 mg/kg intraperitoneally) and then were killed. The anal canal was removed and was transferred quickly to oxygenated Krebs' physiological solution of the following composition (in mmol/L): 118.07 NaCl, 4.69 KCl, 2.52 $CaCl_2$, 1.16 $MgSO_4$, 1.01 $NaH_2PO_4$, 25 $NaHCO_3$ and 11.10 glucose. The large blood vessels and extraneous tissues that contained the external anal sphincter were removed by sharp dissection, and the anal canal was opened and pinned flat with the mucosal side up on a dissecting tray containing oxygenated Krebs' physiological solution. The mucosa was remove by using forceps and fine scissors, and the IAS circular smooth muscle strips (approximately 2 mm wide and 1 cm long) were cut from the lowermost part of the anal canal. Silk suture was tied to both ends of these muscle strips for isometric tension measurements.

Measurement of Isometric Tension

The IAS smooth muscle strips were transferred to temperature-controlled 2-mL muscle baths containing Krebs' solution bubbled continuously with a mixture of 95% $O_2$ and 5% $CO_2$.

The lower end of the muscle strip was tied to the bottom of the muscle bath with the tissue holder, and the other end was attached to an isometric force transducer (model FTO3; Grass Instruments Co., Quincy, Mass.). Isometric tensions of the smooth muscle strips were recorded on a Beckman Dynograph recorder (Beckman Instruments, Schiller Park, Ill.). Initially, 1 g of tension was applied to the muscle strips, which were then allowed to equilibrate for about 1 h with occasional washings. During the equilibration period, strips developed steady tension. Only strips that developed steady tension and relaxed in response to electrical field stimulation were used. Both optimal length and base line of the muscle strips were determined, as described previously. (Chakder, S. et al., J Pharm Exp Therapeut. 266:392–399, 1993; Moummi, C. et al., Am J Physiol. 1988;255:G571–578).

Drug Responses.

TP3654 and CPTA-VIP were chosen as test agents and $VIP_{28}$ as a control. The effect of different concentrations of these agents on resting IAS tension was examined using cumulative concentration responses. After a given concentration-response curve was derived, the muscle strips were washed continuously for 45–60 min before testing for the concentration-response curve of another agent. Maximal relaxation (100%) of the smooth muscle strips was determined after completely relaxing the muscle strips with 5 mmol/L ethylenediaminetetraacetic acid (EDTA).

$^{125}$I-VIP Receptor Displacement Assay with TP3654 and VIP

Colon adenocarcinoma cell line HT-29 was purchased from American Type Culture Collection (ATCC (Manassas, Va.)) and maintained in McCoy's 5A medium containing 10% heat-inactivated fetal bovine serum (FBS), 1% penicillin-streptomycin and 1% minimum essential medium (MEM) vitamins (Mediatech Inc., Herndon, Va.) at 5% $CO_2$ and 37° C.

Confluent cells were collected, washed with 50 mmol/L TrisxHCl buffer (pH 7.5) and then resuspended in 50 mmol/L TrisxHCl buffer (pH 7.5) that contained 5 mmol/L $MgCl_2$, 1 mmol/L $CaCl_2$ and 0.15 mol/L NaCl at 4° C. Approximately $2.5 \times 10^6$ viable cells were dispensed, in triplicate, in several siliconized borosilicate test tubes. Cells were then incubated at 4° C. for 1 h with 40 pmol/L $^{125}$I-VIP (2000 Ci/mmol) in the absence or presence of competitor TP3654 with a known quantity, ranging from $10^{-10}$ mol/L to $10^{-5}$ mol/L. Cells were then centrifuged and washed twice with 1 mL 50 mmol/L TrisxHCl buffer (pH 7.5) at 4° C.; radioactivity bound to the cells was measured using a Packard 5000 series autogamma counter (Packard Instrument Corp., Meriden, Conn.). Similar assays were performed in triplicate in which $VIP_{28}$, instead of TP3654, was used as a competitor. Using the Munsen National Institutes of Health (NIH) ligand-binding program (Bethesda, Md.), binding curves were plotted and half-maximal inhibitory concentrations ($IC_{50}$) were determined.

Tissue Distribution Studies With $^{99m}$Tc-TP3654.

The ability of $^{99M}$Tc-TP3654 to detect human colorectal carcinoma was examined in nude mice.

Human colorectal cancer cells LS 174T (ATCC) were grown in culture and $5 \times 10^6$ viable cells were implanted intramuscularly in the right thighs of athymic NCr nude mice that weighed 20–25 g. Tumors were grown to no more than 1 cm in diameter. Each animal received approximately 700 •Cl of $^{99m}$Tc-TP3654 (1450 Ci/mmol) in 200 •I, of saline through a lateral tail vein. Exact activity injected was determined by measuring the syringe, before and after injection, in a calibrated ionization chamber (Capintech, Ramsey, N.J.). A suitable standard of $^{99m}$Tc was prepared at the time of injection.

At 4 or 24 h later, animals were killed and imaged using a GE STARCAM gamma camera (Milwaukee, Wis.) equipped with a low-energy parallel-hole collimator and a dedicated computer. Tissues were dissected and weighed, and associated radioactivity was counted (Packard 5000 series gamma counter), along with a standard, in duplicate. Results were calculated as percentage injected dose per gram of tissue (% ID/g) and were analyzed by using Student t test.

With $^{125}$I-VIP

Approximately 1 •Ci $^{125}$I-VIP (2000 Ci/mmol) was diluted to 200 •L in 0.05 mol/L phosphate buffer at pH 6.5; 2 •g $VIP_{28}$ was added as a carrier so that the quantity of VIP injected per animal would be the same as for $^{99m}$Tc-TP3654. A tissue distribution study was performed in a manner similar to that for $^{99m}$Tc-TP3654. These data served as positive controls against which $^{99m}$Tc-TP3654 data were compared.

With 99-Tc-G(D)AGG Aba.

G(D)AGG-Aba, the chelating moiety and the spacer, was labeled with $^{99m}$Tc using the same procedure as for $^{99m}$Tc-TP3654. The HPLC retention time for a single-peak $^{99m}$Tc-G(D)AGG-Aba was 6.9 min, distinctly different from the 11.8 min required for $^{99m}$Tc-TP3654. For animal tissue distribution studies, a protocol similar to that for $^{99m}$Tc-TP3654 was followed. Although G(D)AGG-Aba has considerably smaller amino acid residues than TP3654, these data were important because they helped determine whether any cleaving of $^{99m}$Tc-G(D)AGG-Aba had occurred by metabolic interaction with $^{99m}$Tc-TP3654.

Receptor Blocking

Unlabeled VIP-28 or TP3654 (50 •g intravenously) was injected into each of the five LS 174T tumor-bearing nude mice; $^{99m}$Tc-TP3654 (1450 Ci/mmol; 700 •Ci intravenously) was administered 30 min later. The amount of $VIP_{28}$ for 25-g mice (50 •g) was chosen randomly but with the knowledge that a larger amount would be toxic and the assumption that a smaller amount would block only a few receptors that would not be significantly effective in decreasing $^{99m}$Tc-7P3654 uptake. Mice were killed 24 h later, and percentage injected dose per gram of tissues was determined. Data were compared to 24 h distribution in mice (n=5) given 700 •Ci $^{99m}$Tc-TP3654 but not pretreated with unlabeled VIP or TP3654.

Blood Clearance in Rats

Three Sprague-Dawley rats, each weighing approximately 250 g, were injected through a lateral tail vein with 1 mCi $^{99m}$TcTP3654 and serial blood samples were drawn, in triplicate, through the other lateral tail vein at 1, 5, 10, 15 and 30 min and then at 1, 2, 4, 6, 18 and 24 h. Blood samples were weighed, radioactivity was counted with a standard $^{99m}$Tc solution prepared at the time of injection and the percentage injected dose per gram of blood was plotted as a function of time.

Results

The theoretical molecular weight as computed for VIP-Aba-Gly-Gly-(D)-Ala-Gly was 3654.32, whereas the observed molecular weight was 3654.48. In this analog, now called TP3654, no impurities were detected by either HPLC or Sciex APZ ion-spray mass spectrometry. The preparation of $^{99m}$Tc-TP3654 and its proposed structure are presented schematically in FIG. 1. The yield of $^{99m}$Tc-TP3654 was quantitative. The HPLC elution profile (FIG. 2) indicated that, unlike MAG$_3$-VIP or CPTA-VIP, the $^{99m}$Tc-TP3654 preparations were eluted in a single peak (Rt=11.8 min) and that the radiochemical yield was >99%. The HPLC analysis (free $^{99m}$Tc Rt=3.8 min), also indicated that the product was stable for up to 24 h when it was stored at 22° C. and when challenged with 100 molar excess of DTPA, HSA or cysteine for 5 h at 37° C. However, at 24 h of incubation, approximately 11% of the radioactivity was displaced. Colloid content at all times was <5%.

The yields for $^{125}$I-VIP and $^{125}$I-TP3654 were approximately 90% and the retention times for mono-iodo and di-iodo products were 19.3 min and 20.1 min, respectively. The specific activity of the mono-iodo product, free of unlabeled peptide, was approximately 1000 Ci/mmol.

Figure 3:
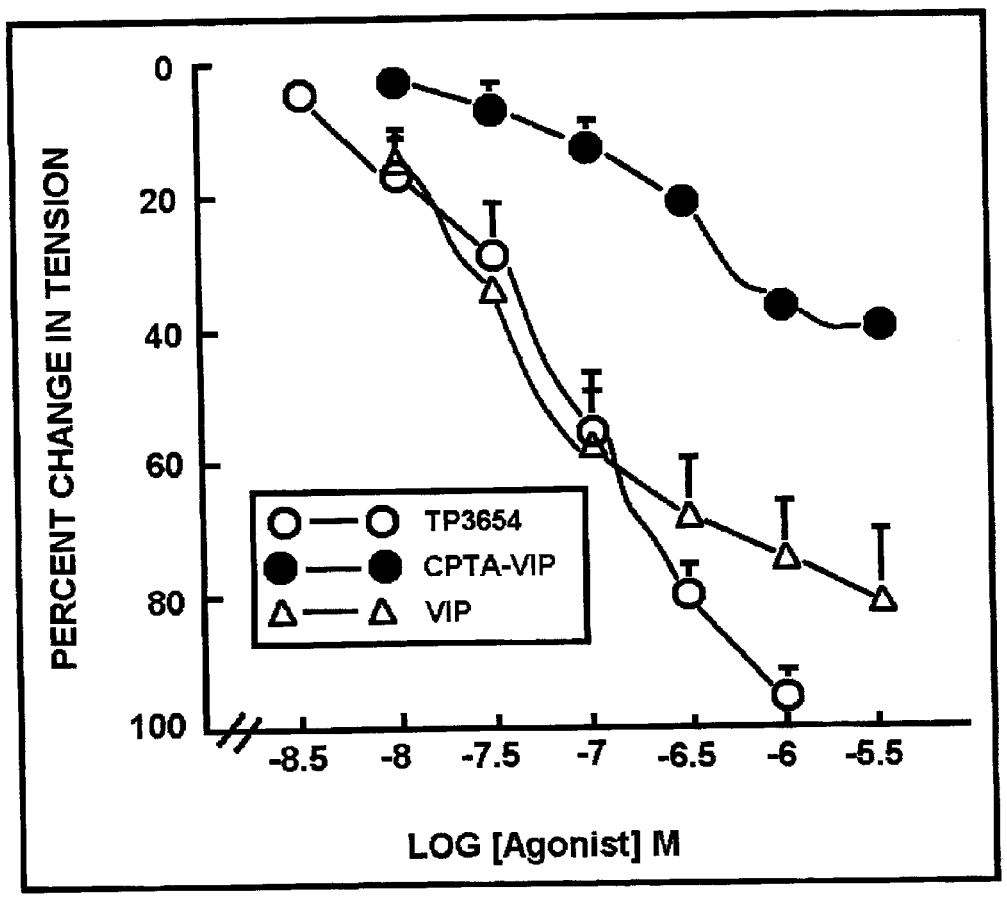
FIG. 3 is a graph of the effect of increasing concentration of VIP$_{28}$, unlabeled TP3654 and CPTA-VIP on resting IAS tension. At $10^{-6}$ mol/L TP3654, 95% muscle relativity was achieved, whereas relativity was approximately 75% with VIP$_{28}$ and 35% with CPTA-VIP at the same concentration.

The results of IAS smooth muscle tissue assays, which indicated that TP3654 was able to exert 95% relaxivity at $10^{-6}$ mol/L, are shown in FIG. 3. At this concentration, relaxivity by VIP$_{28}$ was 80% and relaxivity by CPTA-VIP was 35%. These data confirm previous findings that the biological activity of CPTA-VIP was impaired and that the VEP analog TP3654 was as biologically active as VIP$_{28}$. These data corroborated with the results of experiments in which TP3654 and VIP28 displaced the $^{125}$I-VIP binding of receptors expressed on human colorectal carcinoma cells (HT29). These data are given in FIG. 4. The IC$_{50}$ values, as determined by the NIH ligand-binding program, for both TP3654 and VIP$_{28}$ were approximately 15 nmol/L. These values were consistent with those previously reported for VIP$_{28}$.

In Vivo Evaluation

In Table 1, the tissue distribution data for 4 and 24 h of $^{99m}$Tc-TP3654 and $^{125}$I-VIP are given together with the 24 h tissue distribution of $^{99m}$Tc-G(D)AGG Aba. The distribution of $^{99m}$Tc-G(D)AGG Aba served as a reference and helped to ascertain that the distribution of $^{99m}$Tc-TP3654 was distinctly different from that of the $^{99m}$Tc-chelating moiety. Data indicate that $^{99m}$Tc-TP3654 cleared by renal excretion with 18.99±3.75% ID/g at 4 h and 3.54±0.4% ID/g at 24 h. The liver uptake at these time points was 1.12±0.08% ID/g and 0.33±0.04% ID/g, respectively, followed by the tumor uptake of 0.24±0.08% ID/g and 0.23±0.13% ID/g, respectively. At 24 h after injection, $^{99m}$Tc-TP3654 activity declined significantly in all organs (P<0.01) except the VIP receptor-rich tumor and the lungs (P=0.84 and P=0.78, respectively).

TABLE 1

Biodistribution (% ID/g + SD) of $^{99m}$Tc-TP3654, $^{125}$I-VIP and $^{99m}$Tc-G(D)AGG-Aba at 4 and 24 h Postinjection in Nude Mice Bearing LS174T Colorectal Tumors (n = 5)

| Tissue | $^{99m}$Tc-TP3654 | | $^{125}$I-VIP | | $^{99m}$Tc-G(D)AGG-Aba |
|---|---|---|---|---|---|
| | 4 h*† | 24 h*‡§ | 4 h†‡ | 24 h‡ | 24 h§ |
| Muscle | 0.09 ± 0.01 | 0.04 ± 0.01 | 3.32 ± 0.54 | 0.16 ± 0.03 | 0.01 ± <0+01 |
| Small Intestine | 0.18 ± 0.05 | 0.05 ± 0.01 | 2.12 ± 0.16 | 0.09 ± 0.01 | 0.03 ± 0.01 |
| Heart | 0.10 ± 0.00 | 0.06 ± 0.01 | 1.65 ± 0.07 | 0.09 ± 0.03 | 0.01 ± <0.01 |
| Lung | 0.17 ± 0.01 | 0.16 ± 0.09 | 3.98 ± 2.17 | 0.19 ± 0.10 | 0.03 ± <0.01 |
| Blood | 0.21 ± 0.02 | 0.12 ± 0.02 | 3.40 ± 0.55 | 0.07 ± 0.01 | 0.03 ± <0.01 |
| Spleen | 0.19 ± 0.05 | 0.11 ± 0.02 | 2.13 ± 0.36 | 0.12 ± 0.05 | 0.06 ± 0.03 |
| Kidney | 18.99 ± 3.75 | 3.52 ± .040 | 2.46 ± 0.42 | 0.26 ± 0.03 | 0.20 ± 0.02 |
| Liver | 1.12 ± 0.08 | 0.33 ± 0.04 | 1.98 ± 0.29 | 0.16 ± 0.03 | 0.16 ± 0.02 |
| Tumor | 0.24 ± 0.08 | 0.23 ± 0.13 | 2.15 ± 0.36 | 0.06 ± 0.08 | 0.03 ± <0.01 |
| TIM ratio | 2.73 ± 1.09 | 6.28 ± 3.09 | 0.54 ± 0.39 | 0.38 ± 0.56 | 1.88 ± 0.36 |
| T/B ratio | 1.16 ± 0.29 | 1.98 ± 1.44 | 0.65 ± 0.16 | 0.88 ± 0.16 | 0.77 ± 0.03 |

*Pvalues for 4 h and 24 h $^{99m}$Tc-TP3654 are ≤ 0.01 for all tissues except for lung (P = 0.78), tumor (P = 0.84) and T/B ratio (P = 0.25)
†Pvalues for 4 h $^{99m}$Tc-TP3654 and 4 h $^{125}$I-VIP are ≤0.01 for all tissues
‡Pvalues for 24 h $^{99m}$Tc-TP3654 and 24 h $^{125}$I-VIP are ≤0.01 for all tissues except the heart (P = 0.11) lung (P = 0.55), spleen (P = 0.02) and T/B ratio (P = 0.02).
§Pvalues for 24 h $^{99m}$Tc-TP3654 and $^{99m}$Tc-G(D)AGG-Aba are ≤0.01 for all tissues except for the T/B ratio (P = 0.02).
% ID/g = percentage injected dose per gram; T/M = tumor-to-muscle; T/B tumor-to-blood.

Although the tumor uptake was quantitatively low and remained unchanged, the tumor-to-blood and tumor-to-muscle ratios improved significantly (P<0.01) at 24 h after injection. The tumor uptake was nearly four times higher than that for $^{125}$I-VIP at 24 h after injection (P<0.01). As the time after injection elapsed, $^{125}$I-VIP radioactivity in all tissues, including the tumor and lungs, declined, indicating deiodination from VIP. At 24 h after injection, the $^{99m}$TcG(D)AGG Aba was significantly lower in all tissues than that of $^{99m}$Tc-TP3654 or $^{125}$I-VIP.

Figure 5:
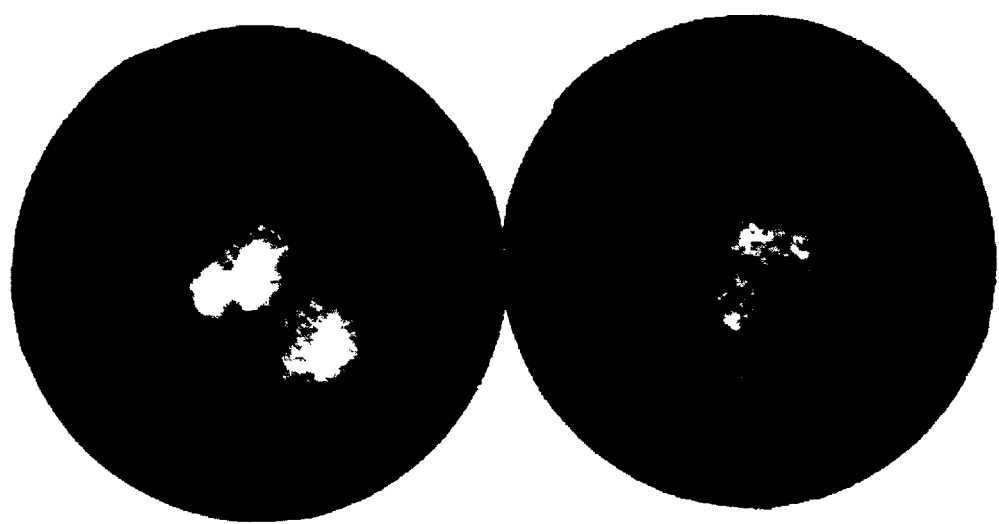
FIG. 5 consists of posterior gamma camera images of nude mice bearing LS174T human colorectal tumor in the right thigh. Both images were obtained 24 h after injection of $^{99m}$Tc-TP3654 (left) and $^{99m}$Tc-G(D)AGG-Aba (right). Tissue distribution is distinctly different. Despite marginal uptake (0.2% ID/g), tumor in the right thigh is delineated with $^{99m}$Tc-TP3654 because of low body background. This tumor is not delineated with $^{99m}$Tc-G(D)AGG-Aba. Both tumors weigh approximately 1 g.

A composite of posterior gamma-camera images of nude mice bearing human colorectal tumor (LS174T), obtained with $^{99m}$Tc-TP3654 and $^{99m}$TC-G(D)AGG-Aba, are given in FIG. 5. The image with $^{99m}$Tc-TP3654 (left) is distinctly different from the one with $^{99m}$Tc-G(D)AGG-Aba (right) and delineates the tumor and both kidneys.

Figure 6:
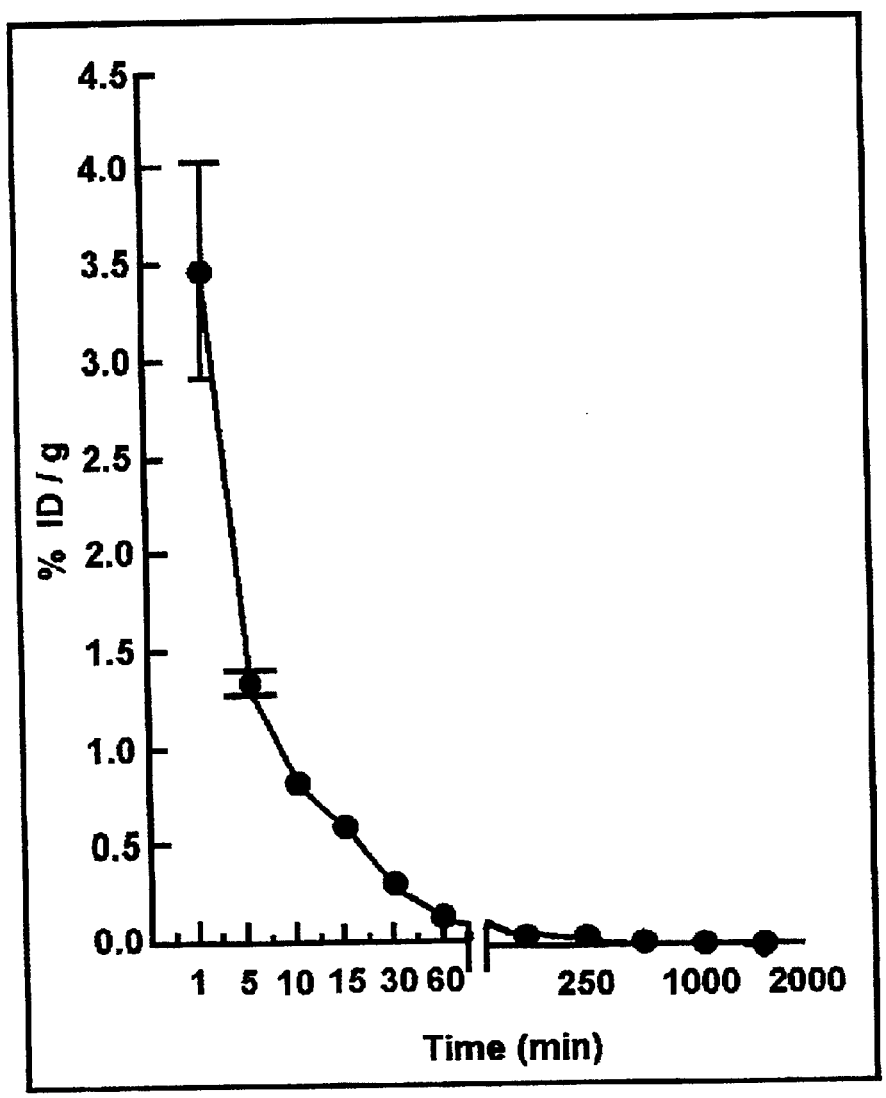
FIG. 6 is a blood clearance curve demonstrating a biphasic behavior of $^{99m}$Tc-TP3654. The $\alpha$-$t_{1/2}$ was approximately 5 min and the $\beta$-$t_{1/2}$ was approximately 120 min.

Results given in Table 2 indicate that in mice treated with unlabeled TP3654 or VIP, the uptake of $^{99m}$Tc-TP3654 decreased in all VIP receptor-rich tissues except the kidneys. The uptake of $^{99m}$Tc-TP3654 in the spleen, liver, muscle and intestine in untreated mice was already low, and even though it was decreased, it was not statistically significantly different after VIP or TP3654 treatment (P=0.07, P=0.07, P=0.42 and P=0.48, respectively). Statistically significant decreases were observed in the heart, lungs, blood and tumor (P<0.01, P<0.02, P<0.01 and P<0.01, respectively). A similar trend was also apparent when mice were treated with unlabeled TP3654. Particularly encouraging was the decreased uptake in the tumor and lungs, which suggested a receptor-blocking phenomenon and indicated that the uptake of $^{99m}$Tc-TP3654 was receptor specific. The increased kidney uptake may have been due to increased metabolites or to any pharmacological effects that may have been exerted by 50 •g VIP or TP3654. The blood clearance curve given in FIG. 6 was biphasic; the •-t $_{1/2}$ was approximately 5 min and the •-t$_{1/2}$ was approximately 120 min. The •-t$_{1/2}$ of 5 min for $^{99m}$Tc-TP3654 obtained in this study was similar to that reported by Bolin et al. The results suggest that the TP3654, the VIP$_{28}$ analog, has retained the receptor specificity of VIP$_{28}$, which does not change when TP3654 is labeled with $^{99m}$Tc.

consistent with those previously reported for VIP$_{28}$. Even more encouraging are the results of the functional IAS assay, shown in FIG. 3. This assay was based on tissue relaxivity, a true functional characteristic of VIP$_{28}$, the and provides confidence in use of TP3654. The VIP receptor density for human colorectal cell line LS 174T is not precisely known and may vary from tumor to tumor. Nonetheless, tumors were clearly delineated with $^{99m}$Tc-TP3654 but not with $^{99m}$Tc-G(D)AGG, the chelate. VIP receptors are ubiquitous

TABLE 2

Tissue Distribution % ID/g ± SD) of $^{99m}$Tc-TP3654 at 24 h in Nude Mice Bearing Human Colorectal Tumors LS174T and Given Intravenously 50 μg TP3654 or 50 μg VIP, 30 min Before the Administration of $^{99m}$Tc-TP3654 (n = 5)

| Tissue | $^{99m}$Tc-TP3654 | TP3654 | Pvalues* | VIP | Pvalues† |
|---|---|---|---|---|---|
| Muscle | 0.04 ± 0.01 | 0.04 ± 0.02 | 0.28 | 0.03 + <0.01 | 0.42 |
| Small intestine | 0.05 ± 0.01 | 0.07 ± 0.02 | 0.13 | 0.04 ± 0.01 | 0.48 |
| Heart | 0.06 ± 0.01 | 0.04 ± 0.00 | <0.01 | 0.02 ± <0.01 | <0.01 |
| Lung | 0.16 ± 0.09 | 0.09 ± 0.03 | 0.08 | 0.05 ± 0.01 | 0.02 |
| Blood | 0.12 ± 0.02 | 0.04 ± 0.01 | <0.01 | 0.04 ± <0.00 | <0.01 |
| Spleen | 0.11 ± 0.02 | 0.16 ± 0.01 | <0.01 | 0.07 ± 0.01 | 0.07 |
| Kidney | 3.52 ± 0.40 | 5.45 ± 1.48 | 0.04 | 12.98 ± 2.11 | <0.01 |
| Liver | 0.33 ± 0.04 | 0.52 ± 0.03 | <0.01 | 0.25 ± 0.06 | 0.07 |
| Tumor | 0.23 ± 0.13 | 0.09 ± 0.02 | <0.01 | 0.07 ± 0.03 | <0.01 |
| T/M ratio | 6.28 ± 3.09 | 2.35 ± 1.01 | 0.02 | 2.45 ± 2.52 | 0.01 |
| T/B ratio | 1.98 ± 1.44 | 2.02 ± 0.52 | 0.05 | 1.54 ± 0.22 | 0.21 |

*Pvalues for 24 h $^{99m}$Tc-TP3654 in mice without and with treatment of 50 μg TP3654.
†Pvalues for 24 h $^{99m}$Tc-TP3654 in mice without and with treatment of 50 μg VIP.
% ID/g = percentage injected dose per gram; VIP = vasoactive intestinal peptide; T/M = tumor-to-muscle; T/B = tumor to blood Discussion $^{111}$In-(DTPA-D-Phe$^{1}$)octreotide has been identified as a useful agent in diagnosis, prognosis and treatment of cancers and has stimulated increasing interest in inherent capabilities of radiolabeled receptor-specific peptides for use in nuclear medicine. Through the original work of Virgolini et al. and Reubi et al., another neuropeptide (VIP$_{28}$) has emerged as a highly potent compound for use in diagnostic imaging. VIP1 and VIP2 receptor subtypes are expressed in higher densities and on more kinds of tumors than somatostatin. These data, together with the excellent physical characteristics of $^{99m}$Tc, prompted the undertaking of the task of preparing $^{99m}$Tc-VIP and evaluating it for functional integrity.

Earlier work, in which VIP was labeled with $^{99m}$Tc by conjugating with BFCAs to His$^{1}$ at the amino terminus of VIP, met with difficulty: multiple radioactive species were formed and a significant amount of biological activity was lost. The current approach has eliminated these drawbacks and offers several advantages.

Figure 4:
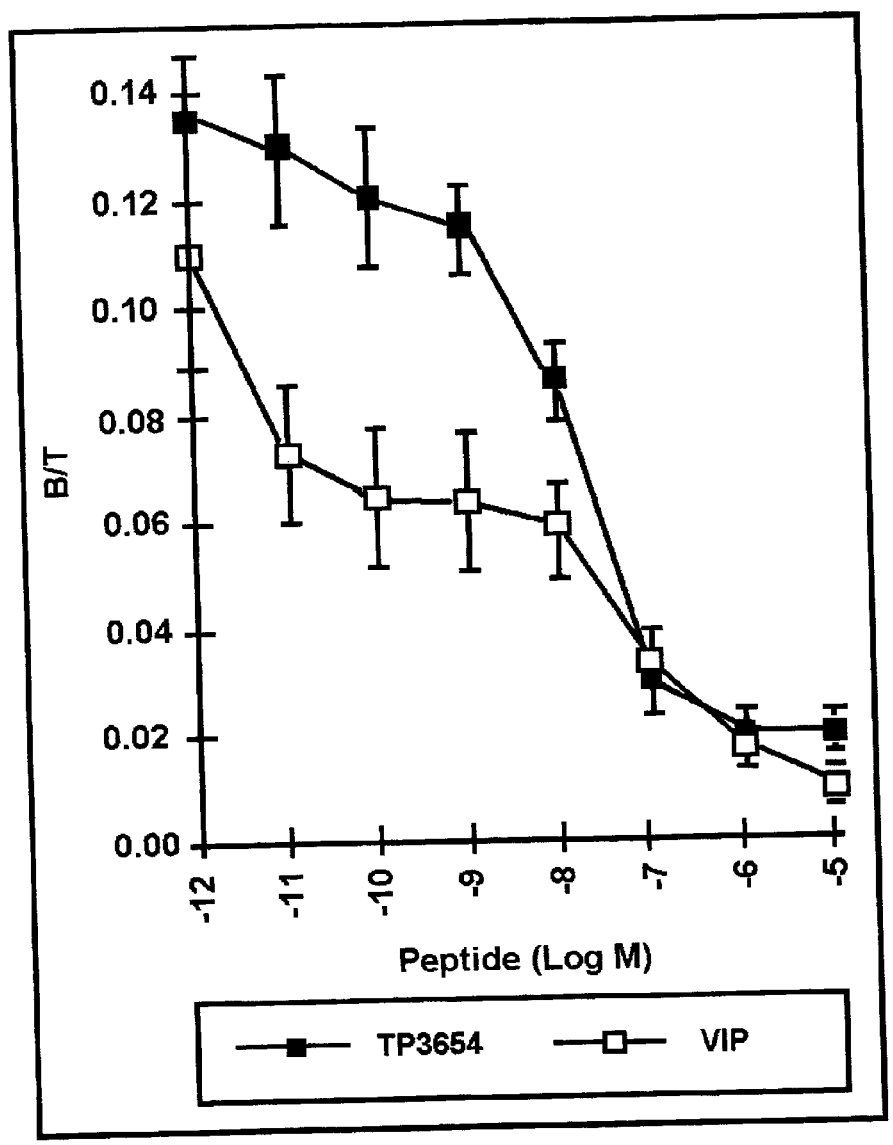
FIG. 4 is a graph of $^{125}$I-VIP displacement curves with unlabeled TP3654 and VIP$_{28}$.

VIP$_{28}$, modified at Asn$^{28}$ by providing a tetrapeptide for strong chelation of $^{9m}$-Tc, results in a single radioactive compound with quantitative yield and without compromising on the biological characteristics of VIP$_{28}$. Using this configuration, TP3654 has been labeled with stable rhenium for nuclear magnetic resonance (NMR) and computer modeling studies. This hybrid peptide approach eliminates the lengthy and frequently inefficacious procedures for synthesizing and conjugating BFCAs, blocking and deblocking certain functional groups and the laborious purifying and characterizing of conjugated peptide. Using the same approach, a straight-chain hexapeptide, a straight-chain heptapeptide and a cyclized octapeptide have been labeled with $^{99m}$Tc. The Aba spacer eliminates any steric hindrance from the chelating moiety and helps preserve the biological activity of the peptide. The chelating moiety can be added to either the carboxy or the amino terminus as needed. Other amino acid combinations to provide the N$_{4}$ configuration also can be chosen. The IC$_{50}$ values for VIP$_{28}$ and TP3654 as determined by data shown in FIG. 4 are 15 nmol/L and are on normal tissues, although their density may be lower than on the malignant cells. Consistently, a large proportion of $^{99m}$Tc-TP3654 was observed in all tissues examined at 4 h after injection (Table 1). At 24 h after injection, this radioactivity decreased in all tissues except in the lungs (P=0.78) and in the tumor (P=0.84). As a result, tumor-to-muscle ratios increased significantly (P=0.04) as the time after injection was prolonged, whereas tumor-to-blood ratios improved only marginally.

The absolute tumor uptake was 0.23±0.13% ID/g, which is considerably less than that with radiolabeled monoclonal antibodies. However, it was significantly greater than $^{125}$I-VIP (0.06±0.08% ID/g; P=0.01). Such low tumor uptakes of other radiolabeled receptor specific peptides have also been observed in mice (0.08% ID/g), in rats (0.04% ID/g) and in humans (0.05% ID/g). In the clinical images, the lung uptake, although not quantified, was very high. In 25-g mice (Table 1), the lung uptake of $^{99m}$Tc-TP3654 at 4 h after injection was 0.17±0.01% ID/g, whereas in 250-g rats, the lung uptake at the same time averaged 0.73±0.12% ID/g.

Although the lung uptake was the same as the tumor in mice on a per unit weight basis (Table 1), lungs were not delineated by scintigraphic imaging (FIG. 5), probably because of their low weight and wide area spread. The maximum uptake of $^{99m}$Tc-TP3654 was in the kidneys. However, this was not contributed by $^{99m}$Tc-G(D)AGG-Aba (0.2±0.02% ID/g; P=0.01) (Table 1), indicating that the chelating moiety was intact and that the renal uptake is caused by the uptake of $^{99m}$Tc-TP3654 or its metabolic products.

Conclusion

A new hybrid peptide technique has been developed for labeling peptides with $^{99m}$Tc. It is applicable to labeling any peptide with $^{99m}$Tc-short or long, cyclized or not—and also is applicable to peptide labeling with radionuclides of rhenium. This method is simple and efficient and has several advantages over conventional bifunctional chelating methods.

Preparation of a Kit for Preparing a Tumor Imaging Agent

A preferred kit formulation is one which will label the composition of formula (I) or (II) instantaneously at room temperature, permits greater than 95% of the added radiolabel to bind to the composition, and has a shelf life of six months or longer.

The kit will be comprised of a carrier and a vial of a composition of formula (I) or (II), stannous chloride, and buffers. The vial will be capable of holding lyophilized reagents as appropriate and will be sealed under nitrogen. Stabilizing agents or anti-oxidants such as EDTA or ascorbic acid may be added to the reagents to increase the shelf life of a kit. Additional vials may contain appropriate reagents including, but not limited to, a buffer, such as 0.05 M phosphate buffer. Antioxidant agents may also be included to prevent oxidation of $Sn^{2+}$ to $Sn^{4+}$. $Sn^{2+}$ is necessary for reduction of $Tc^{7+}$ to lower oxidation states required for chelation.

The present invention may be embodied in other specific forms without departing from the spirit or essential attributes thereof and, accordingly, reference should be made to the appended claims, rather than to the foregoing specification, as indicating the scope of the invention.

What is claimed:

1. A method for imaging tumors in a mammal, said method comprising:
   (a) injecting into said mammal in need of such imaging an effective diagnostic amount of a composition comprising a pharmaceutical carrier and a compound having formula I or II:

M-Z-X$_1$—P—X$_2$ (I)

X$_1$—P—X$_2$-Z-M (II)

wherein:
   M is a four-amino acid radiolabeling moiety complexed to a radionuclide in an N$_4$ configuration;
   Z is 4-aminobutyric acid;
   X$_1$ is from zero to twenty natural or synthetic amino acids;
   P is a peptide having the amino acid sequence His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 1), or an analog or fragment thereof, wherein said analog or fragment retains the biological activity of SEQ.ID.NO: 1; and
   X$_2$ is from zero to twenty natural or synthetic amino acids; and
   (b) scanning said mammal using radioscintigraphic imaging apparatus to image tumors in said mammal.

2. The method according to claim 1 wherein the imaged tumors comprise colorectal carcinoma.

3. The method according to claim 1 wherein the imaged tumors comprise liver metastases.

4. The method according to claim 1 wherein the imaged tumors comprise pancreatic carcinoma.

5. A method for detecting tumors in a mammal comprising
   (a) administering to the mammal an effective diagnostic amount of a compound having formula I or II:

M-Z-X$_1$—P—X$_2$ (I)

X$_1$—P—X$_2$-Z-M (II)

wherein:
   M is a four-amino acid radiolabeling moiety complexed to a radionuclide in an N$_4$ configuration;
   Z is 4-aminobutyric acid;
   X$_1$ is from zero to twenty natural or synthetic amino acids;
   P is a peptide having the amino acid sequence His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 1), or an analog or fragment thereof, wherein said analog or fragment retains the biological activity of SEQ.ID.NO: 1; and
   X$_2$ is from zero to twenty natural or synthetic amino acids; and
   (b) detecting radiolabel localized at the tumor in the mammal.

6. The method according to claim 5 wherein the detected tumors comprise colorectal carcinoma.

7. The method according to claim 5 wherein the detected tumors comprise liver metastases.

8. The method according to claim 5 wherein the detected tumors comprise pancreatic carcinoma.

* * * * *